US006485975B1

(12) United States Patent
Chaturvedi et al.

(10) Patent No.: US 6,485,975 B1
(45) Date of Patent: Nov. 26, 2002

(54) METHOD FOR REGENERATING VIABLE AND FERTILE CITRUS PLANTS BY TISSUE CULTURE FROM EXPLANTS

(75) Inventors: Harish Chandra Chaturvedi, Uttar Pradesh (IN); Sunil Kumar Singh, Uttar Pradesh (IN); Ashok Kumar Sharma, Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/537,249

(22) Filed: Mar. 28, 2000

(51) Int. Cl.$^7$ ................................................. C12N 5/00
(52) U.S. Cl. ....................... 435/420; 435/410
(58) Field of Search .......................................... 435/420

(56) References Cited

PUBLICATIONS

Barliss, M. et al., "In Vitro Plantlet Formation From Citrus Species and Hybrids", 1982, Elsevier Scientific Publishing Co., Amsterdam, vol. 17, pp. 333–341.*
Bhansali, R. et al., "Tissue Culture Propagation of Citrus Trees", 1978, Proceedings of the International Society of Citriculture, pp. 135–140.*
Greno, V. et al., "Influence of Virus and Virus–like Agents on the Development of Citrus Buds Cultured In Vitro", 1988, Kluwer Academic Publishers, vol. 15, pp. 113–124.*

* cited by examiner

Primary Examiner—Bruce R. Campell
Assistant Examiner—Susan B. McCormick
(74) Attorney, Agent, or Firm—Ladas & Parry

(57) ABSTRACT

The invention provides a method for regenerating viable and fertile Citrus plants by tissue culture from explants of field-grown mature trees, said method comprising the steps of incubating the explant in agarified media to develop axillary buds, subculturing the explant alongwith sprouted axillary buds in agarified media, excising the meristem domes along with leaf primordia in another medium to generate shoots, subculturing the meristem-regenerated shoots on filter paper bridge employing a liquid medium in order to obtain healthy shoots of an average length of about 1.5 cm without intervening callusing within a period of 20–25 days, proliferating the meristem-regenerated shoots in agarified media to obtain well-developed shoots, rooting the isolated well-developed shoots in agarified media, transferring the freshly developed roots of *Citrus sinensis* to a different medium while allowing the shoots of *C. aurantifolia* to grow in the same medium for about 15 days to develop tap roots, hardening the rooted shoots ex vitro in a liquid medium, and allowing the shoots to grow in the same medium under incubation conditions, transferring the hardened shoot meristem-raised plants to soilrite in pro-trays for ex vitro growth for about 7 days to ensure 95% to 100% survival of the shoot meristem raised Citrus plants.

11 Claims, No Drawings

METHOD FOR REGENERATING VIABLE AND FERTILE CITRUS PLANTS BY TISSUE CULTURE FROM EXPLANTS

FIELD

The invention provides a method for in-vitro regeneration and proliferation of excised shoot meristems of *Citrus aurantifolis* (Christm.) Swingle and *C. sinensis* (L.) Osbeck.

In essence, the present invention discloses sequential culture conditions, including growth media for in vitro culture of excised shoot meristems taken from field-grown mature trees of *Citrus aurantifolis* (Christm.) Swingle and *C. sinensis* (L.) Osbeck (sweet orange), their regeneration into individual shoots or proliferation, rooting of the isolated meristem-regenerated shoots, hardening of such in vitro-raised plantlets and their successful ex vitro growth.

BACKGROUND

Citrus is the most important fruit of the world, second to grape in commerce and the third important fruit of India so far as production is concerned. However, considering the nutritional value for human health and the large number of products made from it, Citrus may qualify to be the number one fruit of the world.

Citrus plant is vulnerable to infection by a number of pathogens, particularly viruses, viroid, mycoplasma and BLO (bacteria-like organism) besides bacteria and fungi (Spiegel-Roy, P. and Goldschmidt, E. F. 1996. Biology of Citrus, Cambridge University Press, U.K.), which take a heavy toll of citrus fruit production. According to the latest figures available, citrus produce (oranges) in India is less than that produced in Spain in 1992–93.

Also, whilst Spain is the largest exporter of citrus fruit, India exports none (Spiegel-Roy, P. and Goldschmitt, E. F. Biology of Citrus, Cambridge University Press, U.K.), which is paradoxical in view of the far greater citrus orchard area in India as compared with Spain.

The enviable position acquired by Spain in citrus production is mainly due to tissue culture application, particularly micrografting, through which virus-free orchards have been produced, since shoot meristem in citrus is free from viruses and hence, the resulting plant from it is also free from viruses (Murashige, T., Bitters, W. P., Rangan, T. S., Nauer, E. M., Roistacher, C. N. and Holliday, P. B. 1972. A technique of shoot apex grafting and its utilization towards recovering virus-free Citrus clones. Hort Science 7: 118–119; Navarro, L., Roistacher, C. N. and Murashige, T. 1975. Improvement of shoot-tip grafting in vitro for virus-free citrus. J. Amer. Soc. Hort. Sci. 100: 471–479; Navarro, L. 1992. Citrus shoot tip grafting in vitro. In: Biotechnology in Agriculture and Forestry, Vol. 18. Ed. Y. P. S. Bajaj, pp.327–338, Springer-Verlag, Berlin).

Shoot meristem alone, i.e., consisting of apical dome or accompanied by 1, 2 or 3 youngest leaf primordia, measuring 1 mm or less than 1 mm in length comprises meristem culture. It is the best explant for cloning as well as for elimination of pathogens, as its constituent cells are genetically uniform and mostly free from pathogens. Culture of shoot meristem of Citrus is extremely significant, as it has been reported to be free from viruses, viroid, BLO, mycoplasma, bacteria and fungi (Bitters, W. P. and Murashige, T. 1967. A place for tissue culture in citrus research. Calif. Citrograph 52: 226, 228, 270–272, 304, 306; Navarro, L., Civerolo, E./L., Juarez, J. and Garnsey, S. M. 1991. Improving therapy methods for citrus germplasm exchange. In: Proc. Eleventh IOCV Conference, IOCV, Riverside, pp.400–408). Thus, it will result in production of clean stocks of citrus propagules unassociated with undesirable juvenile characters found in nucellars.

Efforts to culture shoot meristem of citrus started during mid sixties, but success could not be achieved (Murashige, T., Bitters, W. P., Rangan, T. S., Nauer, E. M., Roistacher, C. N. and Holliday, P. B. 1972. A technique of shoot apex grafting and its utilization towards recovering virus-free Citrus clones. HortScience 7: 118–119). Since then, despite concerted efforts made world over, success continued to elude citrus meristem culture. As an alternative to shoot meristem culture, micrografting as aseptically grafting shoot meristem of scion onto the epicotyl of a rootstock, has been resorted to in citrus, despite being very tedious and time consuming and requiring great skill and dexterity that too with only about 40% success (Murashige, T., Bitters, W. P., Rangan, T. S., Nauer, E. M., Roistacher, C. N. and Holliday, P. B. 1972. A technique of shoot apex grafting and its utilization towards recovering virus-free Citrus clones is described in HortScience 7: 118–119; Navarro, L., Roistacher, C. N. and Murashige, T. 1975). Improvement of shoot tip grafting in vitro for virus-free Citrus. is described in J. Amer. Soc. Hort. Sci. 100: 471–479; Navarro, L. 1992. Citrus shoot tip grafting in vitro is described in Biotechnology in Agriculture and Forestry, Vol. 18. Ed. Y. P. S. Bajaj, pp.327–338, Springer-Verlag, Berlin. Nevertheless, the micrografting experiments established that by employing meristems of citrus, viruses and other pathogens have been eliminated, resulting in increased fruit production Navarro, L., Civerolo, E. L., Juarez, J. and Garnsey, S. M. 1991. Improving therapy methods for citrus germplasm exchange is described in Proc. Eleventh IOCV Conference, IOCV, Riverside, pp.400–408.

OBJECTS

The main objective of the present invention is to develop a method for production of viable and fertile Citrus plants through in vitro culture of 0.2 to 0.5-mm-long shoot meristems without intervening callusing.

Another objective is to provide growth media and sequential culture conditions, including the physical state of the substratum for optimum regeneration and proliferation of shoot meristems.

Still, other objective is to provide a method for rapid mass production of true-to-type and pathogen-free propagation stocks of both these important scion species.

DETAILED DESCRIPTION

Accordingly, the invention provides a method for regenerating viable and fertile Citrus plants culture from explants of field-grown mature trees of *Citrus aurantifolia* and *C. sinensis*, said method comprising the steps of:

a) cutting an explant from a Citrus plant selected from *Citrus aurantifolia* and *C. sinensis* said explant consisting of single-node stem segments from fresh shoots of field-grown mature trees, b) decontaminating said explant by removing from its surface any contaminant which are harmful to the tissue culture process, c) incubating the surface-sterilized explant at a temperature between 27° C. to 30° C. in the presence of ca.3 klux white fluorescent light for 15 hrs. a day, in agarified medium-A and B respectively for a period ranging between 20–30 days, to develop axillary buds and obtain 70–80% infection-free cultures, d) subculturing the explant of step (c) along with sprouted axillary buds at least 4 times in medium A and B to produce several aseptic fast-growing shoots, e) excising the meristem domes along with youngest 2–3 leaf primordia of length between 0.2–0.5 mm from the aseptically grown shoots and culturing said shoots in medium C at a temperature between 27° C. and 30° C. in the presence of ca.3 klux white fluorescent light for a period of about 15 days to generate shoots of length of ca. 8 mm, f) subculturing the meristem-regenerated shoots on filter paper bridge employing liquid medium-D in order to obtain healthy shoots of an average length of about 1.5 cm without intervening callusing within a period of 20–25 days, g) proliferating the meristem-regenerated shoots by repeated subculture in medium-A and medium-B, respectively to obtain an average of about 10 well-developed shoots within 4 subcultures of 30 days each, h) rooting of the isolated well-developed shoots of $C.$ $aurantifolia$ to the extent of about 100% in 15 days, and of $C.$ $sinensis$ to the extent of about 90% in 25 days, in agarified media-E and F respectively.

i) transferring the freshly developed roots of $C.$ $sinensis$ to medium-G while allowing the shoots of $C.$ $aurantifolia$ to grow in the same medium for a further period of 15 days for development of tap roots, j) hardening the rooted shoots ex vitro in the liquid medium-H for 10 days in a hardening chamber, wherein the relative humidity is regulated from high (ca. 90%) to gradually low (ca. 60%) under ca. 3 klux light intensity from white fluorescent tubes supplemented with light from incandescent lamps at 26° to 28° C. and allowing the shoots to grow in the same medium under incubation conditions for 30 days, k) transferring the hardened shoot meristem-raised plants to soilrite in pro-trays for ex vitro growth at relative humidity of 90% to 60% at a temperature of 27° C. to 30° C. in the presence of white fluorescent light for a period of about 7 days to ensure 95% to 100% survival of the shoot meristem raised Citrus plants.

In an embodiment, the explant from a Citrus plant comprises shoot meristems of length of about 0.2 to 0.5 mm or single node stem segments.

In another embodiment, the explant is decontaminated by surface-sterilizing the nodal stem segments obtained from $C.$ $aurantifolia$ and $C.$ $sinensis,$ washing the said segments with tap water, followed by pre-treating with about 5% "Labolene" solution for 5 minutes, rinsing with distilled water followed by a quick dip in 95% ethanol and surface-sterilizing with 0.1% $HgCl_2$ solution for about 15 minutes and washing the surface-sterilized nodal steam segments thoroughly with sterile distilled water followed by cutting off the affected internodal portions on either side of the node and preparing the explant for inoculation.

The Applicants hereby state that various culture media have been used in the method of for regeneration of citrus plants as described in the foregoing paragraphs.

The various media used in the process of the invention are described hereinbelow and represented in table 1.

Accordingly, medium A comprises:

| INGREDIENTS | CONCENTRATION (mg/L) |
| --- | --- |
| $(NH_4)_2SO_4$ | 250 |
| $(NH_4)_2NO_3$ | 1500 |
| $KNO_3$ | 1500 |
| $KH_2PO_4$ | 150 |
| $CaCl_2.2H_2O$ | 400 |
| $MgSO_4.7H_2O$ | 450 |
| Fe-$Na_2$-EDTA* (ml $1^{-1}$) | 5 |
| $MnSO_4.4H_2O$ | 20 |
| $ZnSO_4.4H_2O$ | 8 |
| $H_3BO_3$ | 6 |
| KI | 0.8 |
| $Na_2MoO_4.2H_2O$ | 0.2 |
| $CuSO_4.5H_2O$ | 0.02 |
| $CoCl_2.6H_2O$ | 0.02 |
| Thiamine-HCl | 0.2 |
| Pyridoxine-HCl | 0.1 |
| Nicotinic acid | 0.5 |
| Ascorbic acid | 10 |
| m-Inositol | 100 |
| Adenine sulphate | 15 |
| BAP | 0.25 |
| IAA | 0.25 |
| Malt Extract | 500 |
| Sucrose (%) | 5 |
| pH | 5.8 |
| Agar (%) | 0.75 |

Further medium B comprises:

| INGREDIENTS | CONCENTRATION (mg/L) |
| --- | --- |
| $KH_2PO_4$ | 250 |
| Adenine sulphate | 25 |
| NAA | 0.5 |
| $(NH_4)_2SO_4$ | 250 |
| $(NH_4)_2NO_3$ | 1500 |
| $KNO_3$ | 1500 |
| $KH_2PO_4$ | 150 |
| $CaCl_2.2H_2O$ | 400 |
| $MgSO_4.7H_2O$ | 450 |
| Fe-$Na_2$-EDTA* (ml $1^{-1}$) | 5 |
| $MnSO_4.4H_2O$ | 20 |
| $ZnSO_4.4H_2O$ | 8 |
| $H_3BO_3$ | 6 |
| KI | 0.8 |
| $Na_2MoO_4.2H_2O$ | 0.2 |
| $CuSO_4.5H_2O$ | 0.02 |
| $CoCl_2.6H_2O$ | 0.02 |
| Thiamine-HCl | 0.2 |
| Pyridoxine-HCl | 0.1 |
| Nicotinic acid | 0.5 |
| Ascorbic acid | 10 |
| m-Inositol | 100 |
| Adenine sulphate | 15 |
| BAP | 0.25 |
| IAA | 0.25 |
| Malt Extract | 500 |
| Sucrose (%) | 5 |
| pH | 5.8 |
| Agar (%) | 0.75 |

Medium C comprises:

| INGREDIENTS | CONCENTRATION (mg/L) |
| --- | --- |
| $(NH_4)_2SO_4$ | 250 |
| $(NH_4)_2NO_3$ | 1500 |
| $KNO_3$ | 1500 |
| $KH_2PO_4$ | 150 |
| $CaCl_2.2H_2O$ | 400 |

-continued

| INGREDIENTS | CONCENTRATION (mg/L) |
|---|---|
| $MgSO_4.7H_2O$ | 450 |
| Fe-$Na_2$-EDTA* (ml $l^{-1}$) | 5 |
| $MnSO_4.4H_2O$ | 20 |
| $ZnSO_4.4H_2O$ | 8 |
| $H_3BO_3$ | 6 |
| KI | 0.8 |
| $Na_2MoO_4.2H_2O$ | 0.2 |
| $CuSO_4.5H_2O$ | 0.02 |
| $CoCl_2.6H_2O$ | 0.02 |
| Thiamine-HCl | 0.2 |
| Pyridoxine-HCl | 0.1 |
| Nicotinic acid | 0.5 |
| Ascorbic acid | 10 |
| m-Inositol | 100 |
| Adenine sulphate | 15 |
| IAA | 0.1 |
| GA | 5 |
| Sucrose (%) | 3 |
| pH | 5.8 |
| L-Glutamine | 25 |
| L-Arginine | 15 |
| L-Asparagine | 10 |
| L-Lysine | 10 |
| L-Cysteine | 10 |

Medium D comprises:

| INGREDIENTS | CONCENTRATION (mg/L) |
|---|---|
| $(NH_4)_2SO_4$ | 250 |
| $(NH_4)_2NO_3$ | 1500 |
| $KNO_3$ | 1500 |
| $KH_2PO_4$ | 150 |
| $CaCl_2.2H_2O$ | 400 |
| $MgSO_4.7H_2O$ | 450 |
| Fe-$Na_2$-EDTA* (ml $l^{-1}$) | 5 |
| $MnSO_4.4H_2O$ | 20 |
| $ZnSO_4.4H_2O$ | 8 |
| $H_3BO_3$ | 6 |
| KI | 0.8 |
| $Na_2MoO_4.2H_2O$ | 0.2 |
| $CuSO_4.5H_2O$ | 0.02 |
| $CoCl_2.6H_2O$ | 0.02 |
| Thiamine-HCl | 0.2 |
| Pyridoxine-HCl | 0.1 |
| Nicotinic acid | 0.5 |
| Ascorbic acid | 10 |
| m-Inositol | 100 |
| Adenine sulphate | 15 |
| BAP | 0.1 |
| IAA | 1 |
| GA | 10 |
| Malt Extract | 100 |
| Sucrose (%) | 3 |
| pH | 5.8 |
| Glycine | 3 |
| L-Glutamine | 25 |
| L-Arginine | 15 |
| L-Asparagine | 10 |
| L-Lysine | 10 |
| L-Cysteine | 10 |

Medium E comprises:

| INGREDIENTS | CONCENTRATION (mg/L) |
|---|---|
| $(NH_4)_2SO_4$ | 100 |
| $(NH_4)_2NO_3$ | 300 |
| $KNO_3$ | 500 |
| $KH_2PO_4$ | 150 |

-continued

| INGREDIENTS | CONCENTRATION (mg/L) |
|---|---|
| $CaCl_2.2H_2O$ | 100 |
| $MgSO_4.7H_2O$ | 100 |
| Fe-$Na_2$-EDTA* (ml $l^{-1}$) | 5 |
| $MnSO_4.4H_2O$ | 20 |
| $ZnSO_4.4H_2O$ | 8 |
| $H_3BO_3$ | 6 |
| KI | 0.8 |
| $Na_2MoO_4.2H_2O$ | 0.2 |
| $CuSO_4.5H_2O$ | 0.02 |
| $CoCl_2.6H_2O$ | 0.02 |
| Thiamine-HCl | 0.2 |
| Pyridoxine-HCl | 0.1 |
| Nicotinic acid | 0.5 |
| Ascorbic acid | 10 |
| Adenine sulphate | 5 |
| IPA | 0.125 |
| IBA | 0.125 |
| Chlorogenic acid | 1 |
| Sucrose (%) | 3 |
| pH | 5.8 |
| Agar (%) | 0.75 |

Medium F comprises:

| INGREDIENTS | CONCENTRATION (mg/L) |
|---|---|
| $(NH_4)_2SO_4$ | 200 |
| $(NH_4)_2NO_3$ | 500 |
| $KNO_3$ | 500 |
| $KH_2PO_4$ | 250 |
| $CaCl_2.2H_2O$ | 200 |
| $MgSO_4.7H_2O$ | 300 |
| Fe-$Na_2$-EDTA* (ml $l^{-1}$) | 5 |
| $MnSO_4.4H_2O$ | 20 |
| $ZnSO_4.4H_2O$ | 8 |
| $H_3BO_3$ | 6 |
| KI | 0.8 |
| $Na_2MoO_4.2H_2O$ | 0.2 |
| $CuSO_4.5H_2O$ | 0.02 |
| $CoCl_2.6H_2O$ | 0.02 |
| Thiamine-HCl | 2.5 |
| Pyridoxine-HCl | 0.5 |
| Nicotinic acid | 0.5 |
| Riboflavin | 0.1 |
| Folic acid | 0.1 |
| d-Biotin | 0.1 |
| Ascorbic acid | 5 |
| Adenine sulphate | 5 |
| IAA | 1 |
| NAA | 0.5 |
| IPA | 0.5 |
| Chlorogenic acid | 1 |
| Sucrose (%) | 5 |
| pH | 5.8 |
| Agar (%) | 0.75 |
| Glycine | 3 |
| L-Arginine | 15 |

Medium G comprises:

| INGREDIENTS | CONCENTRATION (mg/L) |
|---|---|
| $(NH4)_2NO_3$ | 500 |
| $KNO_3$ | 250 |
| $KH_2PO_4$ | 125 |
| $Ca(NO_3)_2.4H_2O$ | 500 |
| $MgSO_4.7H_2O$ | 250 |
| Fe-$Na_2$-EDTA* (ml $l^{-1}$) | 3 |
| $MnSO_4.4H_2O$ | 20 |
| $ZnSO_4.4H_2O$ | 8 |

-continued

| INGREDIENTS | CONCENTRATION (mg/L) |
|---|---|
| $H_3BO_3$ | 6 |
| KI | 0.8 |
| $Na_2MoO_4.2H_2O$ | 0.2 |
| $CuSO_4.5H_2O$ | 0.02 |
| $CoCl_2.6H_2O$ | 0.02 |

Medium H comprises:

| INGREDIENTS | CONCENTRATION (mg/L) |
|---|---|
| $(NH4)_2NO_3$ | 500 |
| $KNO_3$ | 250 |
| $KH_2PO_4$ | 125 |
| $Ca(NO_3)_2.4H_2O$ | 500 |
| $MgSO_4.7H_2O$ | 250 |
| Fe—$Na_2$-EDTA* (ml $1^{-1}$) | 3 |
| $MnSO_4.4H_2O$ | 20 |
| $ZnSO_4.4H_2O$ | 8 |
| $H_3BO_3$ | 6 |
| KI | 0.8 |
| $Na_2MoO_4.2H_2O$ | 0.2 |
| $CuSO_4.5H_2O$ | 0.02 |
| $CoCl_2.6H_2O$ | 0.02 |

It would be pertinent to note that the various combination of the media hereinlisted would be apparent to those skilled in the art. Such media are deemed to fall within the scope of the present invention.

The tissue culture method for regenerating viable and fertile Citrus plants from field grown trees of C. aurantifolia and C. sinensis is described in further detail as under:

a) excising the single-node stem segments from fresh growth of shoots wherein the said method of field-grown mature elite trees of C. aurantifolia and C. sinensis during the month of February, b) surface-sterilizing the nodal stem segments of both the Citrus species by washing the said segments with tap water, followed by pre-treating with about 5% "Labolene", a neutral liquid detergent from Glaxo India Ltd. solution for 5 minutes, then rinsing with single distilled water followed by a quick dip in 95% ethanol and surface-sterilizing with 0.1% $HgCl_2$ solution for about 15 minutes and washing the surface-sterilized nodal steam segments thoroughly with sterile distilled water followed by cutting off the affected internodal portions on either side of the node and preparing the explants for inoculation;

c) incubating the surface-sterilized explants of C. aurantifolia and C. sinensis under ca. 3 klux white fluorescent light for 15 h a day at 27°±1° C. temperature in agarified medium-A and medium-B respectively, for a period ranging between 20–30 days for axillary bud sprouting to obtain 70–80% infection-free cultures of C. aurantifolia and C. sinensis, d) subculturing the explants along with sprouted axillary buds for at least 4 times in the same respective media as in step (c) to produce enormous number of aseptically fast-growing shoots, e) excising the meristem domes along with youngest 2–3 leaf primordia ranging in length between 0.2–0.5 mm from the aseptically grown shoots followed by their culture on the liquid medium-C under the same controlled light and temperature conditions as in step (c) at least for a period of 15 days to let them attain a length of ca. 8 mm, f) subculturing the meristem-regenerated shoots on filter paper bridge employing liquid medium-D in order to obtain healthy shoots of an average length of about 1.5 cm without intervening callusing within a period of 20–25 days, g) proliferating the meristem-regenerated 1.5-cm-long shoots of C. aurantifolia and C. sinensis by repeated subculture in medium-A and medium-B, respectively to obtain well-developed shoots to the extent of an average 10 shoots and 6 shoots, respectively, within 4 subcultures of 30 days each, h) rooting of the isolated well-developed shoots of C. aurantifolia to the extent of 100% in 15 days, and of C. sinensis to the extent of 90% in 25 days, in agarified media-E and F respectively.

i) transferring the just rooted of C. sinensis to medium-G while those of C. aurantifolia were left to grow in the same medium for a further period of 15 days in order to obtain almost a tap root-like system.

j) hardening the rooted shoots ex vitro in the liquid medium-H for 10 days in a hardening chamber, where the R.H. being regulated from high (ca. 900/%) to gradually low (ca. 60%) under ca. 3 klux light intensity from white fluorescent tubes supplemented with light from incandescent lamps at 27°±1° C. and allowing to grow the rooted shoots further in the same medium and incubation conditions for another 30 days.

k) transferring the hardened shoot meristem-raised plants to soilrite in pro-trays for ex vitro growth under the same humidity regime and incubation conditions as stated in step (j) for 7 days to obtain their 95% to 100% survival.

It took ca. 18 months to obtain well-developed healthy plants of an average height of 15 cm in potted soil, after the first establishment in aseptic culture of nodal explants taken from field-grown trees of Citrus.

The invention is illustrated in detail by the following examples which should be construed to limit the scope of the invention in any manner.

Experiment 1

Proliferation of Isolated Shoots Obtained from Regenerated Nodal Stem Segments of Mature Field-grown Trees of Citrus aurantifolis and C. sinensis The earlier investigations performed in this Laboratory on citrus tissue culture, in which it has been established that amongst cytokinins, BAP was the most effective cytokinin for induction of shoot bud differentiation at its moderate concentration (0.25 or 0.5 mg $1^{-1}$) used along with a low concentration (0.1–0.5 mg $1^{-1}$) of NAA or IAA (Chaturvedi, H. C. and Mitra, G. C. 1974. Clonal propagation of citrus from somatic callus cultures. HortScience 9: 118–120). Therefore, preliminary experiments were conducted by taking the same cytokinin and auxins for inducing proliferation of shoots of Citrus aurantifolis and C. sinensis, which revealed that much variation in response was effected by different concentrations of BAP used with 0.25 mg $1^{-1}$ IAA and 0.5 mg $1^{-1}$ NAA, respectively. Proliferation of isolated shoots was obtained in presence of BAP and an auxin, LAA or NAA employing the medium-A (Table I) for C. aurantifolia, and medium-B (Table I) for C. sinensis, but not vice-versa, where both media A and B, devoid of growth hormones comprised the basal media. It was observed that while IAA used together with BAP was more conducive to proliferation of shoots of C. aurantifolia, the NAA was more effective in case of C. sinensis. Responses of the isolated shoots to some selected combinations of BAP with IAA or NAA are given in the Table 1, which lead to the selection of specific nutrient media for optimum proliferation of shoots of these two Citrus species.

The maximum number of offshoots produced per explant of a shoot tip of *C. aurantifolia* was 7 in 0.75 mg $l^{-1}$ BAP and 0.25 mg $l^{-1}$ IAA, however, the shoots not only were restricted in growth, but also substantial intervening callus was formed. Similarly, in the concentrations of 0.5 and 1.0 mg $l^{-1}$ BAP, particularly the second aspect of response remained equally prominent, i.e., growth restriction of offshoots and intervening callusing during their differentiation. In 0.25 mg $l^{-1}$ BAP, the number of offshoots formed was more than that formed in its rest of the concentrations except 0.75 mg $l^{-1}$, while the shoots were also fast growing and were differentiated without any intervening callusing, which response resulted in the formation of far greater number of well-developed shoots per culture, desirable for root induction. Thus, the 0.25 mg $l^{-1}$ concentration of both BAP and IAA was selected comprising the medium-A for proliferation of isolated shoots originally regenerated from nodal stem segments of mature field-grown trees of *C. aurantifolia*.

Likewise, 0.25 mg $l^{-1}$ concentration of BAP and 0.5 mg $l^{-1}$ of NAA were selected comprising the medium-B for optimum proliferation of shoots of *C. sinensis* in view of the same two criteria, viz., moderately high number of offshoot production with good growth and their differentiation without any intervening callusing. However, the number of offshoots produced, i.e., 2.6 was remarkably less than that produced in case of *C. aurantifolia*, i.e., 5.8 in the respective optimum treatments, albeit the regenerated offshoots showed slightly better growth than those of *C. aurantifolia*.

The shoots regenerated in both the Citrus species were normal in appearance with a good development of green foliage.

Experiment 2
Growth of Excised Shoot Meristems of *Citrus aurantifolis* and *C. sinensis*

Since for growth, an excised shoot meristem may require exogenous supply of mainly three growth hormones, viz., a cytokinin, an auxin and a gibberellin, these were provided individually at 3 concentrations (mg $l^{-1}$) each and in certain combinations as given below using the medium-C (Table I) devoid of IAA and GA as the basal medium: 0.1 BAP; 0.25 BAP; 0.5 BAP; 0.1 IAA; 0.25 IAA; 0.5 IAA: 5 GA; 10 GA; 15 GA; 0.1 BAP+0.1 IAA; 0.25 BAP+0.1 IAA; 0.5 BAP+0.1 IAA; 5 GA+0.1 IAA; 10 GA+0.1 IAA and 15 GA+0.1 IAA.

Shoot meristems, measuring 0.2–0.5 mm in length did not survive in the nutrient agar alone or having any of the 3 growth hormones individually, albeit the necrosis of shoot meristem was slightly delayed by a few days (10–15) in the individual presence of BAP, particularly in its lower concentration of 0.1 mg $l^{-1}$, but a tendency towards abnormal growth or callusing was apparent, more so in its 0.5 mg $l^{-1}$ concentration. Furthermore, the shoot meristems remained fresh with a little increase in their length in lower concentrations of IAA (0.1 mg $l^{-1}$) or GA (5 mg $l^{-1}$).

In the next step, on the basis of the responses obtained, shoot meristems were cultured in all the afore-said 3 concentrations of BAP (0.1, 0.25 and 0.5 mg $l^{-1}$) or GA (5, 10 and 15 mg $l^{-1}$) along with 0.1 mg $l^{-1}$ IAA. Whilst the shoot meristems registered some growth in GA treatments, they became abnormally thick in BAP treatments, with a tendency of callusing at its higher concentrations. Hence, for initial growth of shoot meristems, all the 3 concentrations of GA with 0.1 mg $l^{-1}$ IAA were tested for their regeneration promoting effect on shoot meristems cultured on nutrient agar, where 5 mg $l^{-1}$ GA along with 0.1 mg $l^{-1}$ IAA was found to be the optimum. In this treatment, growth of meristem on nutrient agar as well as in liquid medium using filter paper bridge was compared. Shoot meristems grew far better on filter paper bridge than on nutrient agar in the same treatment (table 3). However, the shoot meristems after a little growth during 30 days' incubation, on subculture in the respective culture conditions (nutrient agar and liquid medium with filter paper bridge) failed to register further growth.

The shoot meristems, which were restricted in their further growth even on filter paper bridge with the same liquid medium except having higher concentrations of IAA (1 mg $l^{-1}$) and GA (10 mg $l^{-1}$) also did not grow further unless 0.1 mg $l^{-1}$ BAP was additionally present, while incorporation of 100 mg $l^{-1}$ malt extract was beneficial for general health of meristem-regenerated shoots, such a formulation comprised the medium-D (Table I). Higher or lower than 0.1 mg $l^{-1}$ concentrations of BAP were not conducive to normal growth of shoot meristems.

Experiment 3
Root Induction in Meristem-regenerated Shoots of *Citrus aurantifolia* and *C. sinensis*

The meristem-regenerated well-developed shoots of *C. aurantifolia* easily rooted in medium-E (Table I) selected on the basis of the formulations used earlier during the investigations on Citrus tissue culture in this Laboratory (Chaturvedi, H. C. 1979. Tissue culture of economic plants. In: Progress in Plant Research. Eds. T. N. Khoshoo and P. K. K. Nair, Today and Tomorrow's Publisher, New Delhi, Vol.1, pp.265–288; Chaturvedi, H. C. and Sharma, A. K. 1988. Citrus tissue culture. In: Proc. Natl. Seminar on Plant Tissue Culture, I.C.A.R., New Delhi, pp.36–46). The basic differences of the root inducing media from the shoot proliferation media of Citrus are, comparatively lower concentrations of nitrogen, calcium and magnesium in the former. Hundred percent rooting was obtained in *C. aurantifolia* in the presence of 0.25 mg $l^{-1}$ NAA, IBA, IAA or IPA, or 0.125 mg $l^{-1}$ each of any of the two auxins used with 1 mg $l^{-1}$ chlorogenic acid, albeit the desirable rooting (1 or 2 roots without intervening callusing) was obtained in 0.125 mg $l^{-1}$ each of IBA and IPA with 1 mg $l^{-1}$ chlorogenic acid. However, the meristem-regenerated shoots of *C. sinensis* did not root in any of these treatments. Even its shoots raised from seedling explants have been reported to be intractable-to-root in vitro (Duran-vila, N., Ortega, V. and Navarro, L. 1989. Morphogenesis and tissue cultures of three citrus species. Plant Cell, Tissue and Organ Culture, 16: 123–133). Hence, experiments were conducted for inducing a good percentage of desirable rooting in the meristem-regenerated shoots of *C. sinensis*.

The medium-E, which was found effective for inducing desirable rooting in a number of Citrus species, including its rootstocks, when was found deficient for promoting root induction in the presence of multiple combinations of auxins, viz., IAA. IPA, IBA and NAA without or with phenolic acids, namely, phloroglucinol and chlorogenic acid, it was variously modified. The modifications included, increase in the concentrations of thiamine-HCl, pyridoxine-HCl and nicotinic acid to 2.5, 0.5 and 0.5 mg $l^{-1}$, respectively, addition of some other root promoting vitamins, like, riboflavin, folic acid and d-biotin at the concentration of 0.1 mg $l^{-1}$ each as also 15 mg $l^{-1}$ L-arginine.

The rooting responses of well-developed isolated shoots of *C. sinensis* to various auxins used without and with phenolic acids employing the medium-E (Table I) devoid of auxins and the phenolic acid as the basal medium, are presented in Table 3. A combination of three auxins, namely, IAA, NAA and IPA along with a phenolic acid, namely, chlorogenic acid or phloroglucinol was essential for root induction. Of the two phenolic acids, chlorogenic acid was more effective for its synergistic effect with auxins in root induction. Furthermore, incubation of cultures for the initial 7 days in the total dark followed by their incubation under normal culture conditions, as mentioned before, greatly enhanced the rooting percentage over their corresponding cultures incubated under normal culture conditions ab initio.

In the optimum concentration of 1 mg $l^{-1}$ of IAA and 0.5 mg $l^{-1}$ each of NAA and IPA along with 1 mg $l^{-1}$ chlorogenic acid, besides other constituents, as the medium F and an incubation for the initial 7 days in the total dark resulted in the differentiation of root primordia in isolated shoots within 25 days, which developed into normal roots on transfer to medium-G having a lower concentration of only one auxin, namely, 0.25 mg $l^{-1}$ IAA with 1 mg $l^{-1}$ chlorogenic acid (Table I).

It took about 40 days for obtaining well-developed roots without intervening callusing in 90% meristem-regenerated shoots of *C. sinensis* with their sequential culture in medium-F and medium-G.

TABLE I

COMPOSITIONS OF MEDIA USED
(Concentrations in mg $l^{-1}$)

| INGREDIENTS | A | B | C | D | E | F | G | H |
|---|---|---|---|---|---|---|---|---|
| $(NH_4)_2SO_4$ | 250 | 250 | 250 | 250 | 100 | 200 | 200 | — |
| $NH_4NO_3$ | 1500 | 1500 | 1500 | 1500 | 300 | 500 | 500 | 500 |
| $KNO_3$ | 1500 | 1500 | 1500 | 1500 | 500 | 500 | 500 | 250 |
| $KH_2PO_4$ | 150 | 250 | 150 | 150 | 150 | 250 | 250 | 125 |
| $CaCl_2.2H_2O$ | 400 | 400 | 400 | 400 | 100 | 200 | 200 | — |
| $Ca(NO_3)_2.4H_2O$ | — | — | — | — | — | — | — | 500 |
| $MgSO_4.7H_2O$ | 450 | 450 | 450 | 450 | 100 | 300 | 300 | 250 |
| Fe—$Na_2$—EDTA* (ml $l^{-1}$) | 5 | 5 | 5 | 5 | 5 | 5 | 5 | 3 |
| $MnSO_4.4H_2O$ | 20 | 20 | 20 | 20 | 20 | 20 | 20 | 20 |
| $ZnSO_4.4H_2O$ | 8 | 8 | 8 | 8 | 8 | 8 | 8 | 8 |
| $H_3BO_3$ | 6 | 6 | 6 | 6 | 6 | 6 | 6 | 6 |
| KI | 0.8 | 0.8 | 0.8 | 0.8 | 0.8 | 0.8 | 0.8 | 0.8 |
| $Na_2MoO_4.2H_2O$ | 0.2 | 0.2 | 0.2 | 0.2 | 0.2 | 0.2 | 0.2 | 0.2 |
| $CuSO_4.5H_2O$ | 0.02 | 0.02 | 0.02 | 0.02 | 0.02 | 0.02 | 0.02 | 0.02 |
| $CoCl_2.6H_2O$ | 0.02 | 0.02 | 0.02 | 0.02 | 0.02 | 0.02 | 0.02 | 0.02 |
| Thiamine-HCl | 0.2 | 0.2 | 0.2 | 0.2 | 0.2 | 2.5 | 2.5 | — |
| Pyridoxine-HCl | 0.1 | 0.1 | 0.1 | 0.1 | 0.1 | 0.5 | 0.5 | — |
| Nicotinic acid | 0.5 | 0.5 | 0.5 | 0.5 | 0.5 | 0.5 | 0.5 | — |
| Riboflavin | — | — | — | — | — | 0.1 | 0.1 | — |
| Folic acid | — | — | — | — | — | 0.1 | 0.1 | — |
| d-Biotin | — | — | — | — | — | 0.1 | 0.1 | — |
| Ascorbic acid | 10 | 10 | 10 | 10 | 10 | 5 | 5 | — |
| m-Inositol | 100 | 100 | 100 | 100 | — | — | — | — |
| Glycine | — | — | 3 | 3 | — | 3 | 3 | — |
| L-Glutamine | — | — | 25 | 25 | — | — | — | — |
| L-Arginine | — | — | 15 | 15 | — | 15 | 15 | — |
| L-Asparagine | — | — | 10 | 10 | — | — | — | — |
| L-Lysine | — | — | 10 | 10 | — | — | — | — |
| L-Cysteine | — | — | 10 | 10 | — | — | — | — |
| Adenine sulphate | 15 | 25 | 15 | 15 | 5 | 5 | 5 | — |
| BAP | 0.25 | 0.25 | — | 0.1 | — | — | — | — |
| IAA | 0.25 | — | 0.1 | 1 | — | 1 | 0.25 | — |
| NAA | — | 0.5 | — | — | — | 0.5 | — | — |
| IPA | — | — | — | — | 0.125 | 0.5 | — | — |
| IBA | — | — | — | — | 0.125 | — | — | — |
| Chlorogenic acid | — | — | — | — | 1 | 1 | 1 | — |
| GA | — | — | 5 | 10 | — | — | — | — |
| Malt Extract | 500 | 500 | — | 100 | — | — | — | — |
| Sucrose (%) | 5 | 5 | 3 | 3 | 3 | 5 | 5 | — |
| pH | 5.8 | 5.8 | 5.8 | 5.8 | 5.8 | 5.8 | 5.8 | — |
| Agar (%) | 0.75 | 0.75 | — | — | 0.75 | 0.75 | 0.75 | — |

*Fe—$Na_2$—EDTA was prepared by dissolving 557 mg $FeSO_4.7H_2O$ (Ferrous sulphate) in 100 ml warm solution containing 745 mg of $Na_2$—EDTA in double distilled water.
Abbreviations: BAP: 6-benzylaminopurine; Fe—$Na_2$—EDTA: Ferric-ethylene-diamine-tetraacetic acid (disodium); GA: gibberellic acid; IAA: indole-3-acetic acid; IBA: indole-3-butyric acid; IPA: indole-3-propionic acid; NAA: α-naphthalene-acetic acid

TABLE II

Effect of different concentrations of BAP (used with an auxin) on proliferation of isolated shoots of *Citrus aurantifolia* and *C. sinensis*. Culture period: 30 days

*Citrus aurantifolia*

| BAP (0.25 IAA) Conc. mg l$^{-1}$ | No. of off-shoots regenerated* | Growth of regenerated shoots Length in cm* | Condition of shoots |
|---|---|---|---|
| 0.1 | 3.6 ± 0.40 | 1.44 ± 0.14 | A few well-developed shoots, rest with necrosed leaves |
| 0.25 | 5.8 ± 0.58 | 1.40 ± 0.13 | Well-developed sturdy shoots with well formed green leaves |
| 0.5 | 5.4 ± 1.02 | 0.99 ± 0.10 | Shoots thin and with narrow leaves |
| 0.75 | 7.0 ± 0.44 | 0.86 ± 0.08 | Shoots thin and with narrow leaves |
| 1.0 | 5.6 ± 1.40 | 0.76 ± 0.10 | Weak shoots with very narrow leaves and restricted in growth |

*C. sinensis*

| BAP (0.5 NAA) Conc. mg l$^{-1}$ | No. of off-shoots regenerated* | Growth of regenerated shoots Length in cm* | Condition of shoots |
|---|---|---|---|
| 0.1 | 1.8 ± 0.37 | 1.16 ± 0.27 | A few well-developed shoots, rest with necrosed leaves |
| 0.25 | 2.6 ± 0.24 | 1.65 ± 0.20 | Well-developed stout shoots with well formed expanded leaves |
| 0.5 | 3.4 ± 0.44 | 1.08 ± 0.12 | Well-developed stout shoots with well formed expanded leaves |
| 0.75 | 3.2 ± 0.73 | 0.78 ± 0.10 | Thin shoots with less developed leaves and restricted in growth |
| 1.0 | 2.0 ± 0.31 | 0.75 ± 0.08 | Thin shoots with less developed leaves and restricted in growth |

*Average of 5 replicate cultures ± S.E.

TABLE III

Growth of 0.5 mm-long excised shoot meristems of *Citrus aurantifolia* and *C. sinensis* on nutrient agar and on filter paper bridge using liquid nutrient medium in the optimum treatment containing 5 mg l$^{-1}$ GA and 0.1 mg l$^{-1}$ IAA

| Medium C | Length (mm) of shoot meristems at different incubation periods (days)* | | |
|---|---|---|---|
| | 15 | 30 | 45 |
| *Citrus aurantifolia* | | | |
| Agarified | 7.0 ± 0.70 | 8.2 ± 0.66 | 8.2 ± 0.66 |
| Liquid with filter paper bridge | 8.2 ± 0.80 | 12.6 ± 1.86 | 13.2 ± 1.80 |
| *C. sinensis* | | | |
| Agarified | 7.6 ± 0.50 | 8.6 ± 0.60 | 8.6 ± 0.60 |
| Liquid with filter paper bridge | 9.4 ± 2.67 | 12.8 ± 2.59 | 13.6 ± 2.29 |

*Average of 5 replicate cultures ± S.E.

TABLE IV

Effect of different auxins, phenolic acids and dark incubation on root induction in excised meristem regenerated isolated shoots of *Citrus sinensis*. Conc. mg l$^{-1}$

| Auxins | | | | Phenolic acids | | Incubation in total dark for initial 7 days | Rooting* |
|---|---|---|---|---|---|---|---|
| IAA | NAA | IPA | Picloram | Chlorogenic acid | Phloroglucinol | | % |
| 0.5 | – | – | – | – | – | – | – |
| 0.5 | 0.5 | – | – | – | – | – | – |
| 0.5 | 0.5 | 0.5 | – | – | – | – | – |
| 0.5 | 0.5 | 0.5 | – | 1 | – | – | 10 |
| 1 | 0.5 | 0.5 | – | 1 | – | – | 30 |
| 1 | 0.5 | 0.5 | – | – | 1 | – | 10 |
| 1 | 0.5 | 0.5 | – | 1 | – | + | 90 |
| 1 | 0.5 | 0.5 | – | 0.5 | 0.5 | + | 20 |
| 1 | – | 0.5 | – | 1 | – | + | – |
| 1 | 0.5 | – | – | 1 | – | + | – |
| – | 0.5 | 0.5 | – | 1 | – | + | – |
| – | 0.5 | 0.5 | 0.5 | 1 | – | + | – |
| – | 0.5 | 0.5 | 1 | 1 | – | + | – |

*Average of 10 replicate cultures

Advantages

The main advantages of the present invention are:
1. The protocol developed will afford rapid production of cloned and pathogen-free plants of elite trees of two commercially most important Citrus species even if the mother trees were diseased.
2. Establishment of disease-free citrus orchards will lead to not only self-sufficiency by increased fruit production, but also export promotion through a strong Citrus Industry of International standards.

What is claimed is:

1. A method for regenerating viable and fertile Citrus plants by tissue culture from explants of field-grown mature trees said method comprising the steps of:
   (a) cutting explants selected from fresh shoots of field-grown mature trees of a citrus species selected from the group consisting of *C. aurantifolia* and *C. sinensis;*
   (b) decontaminating the said explants by surface sterilization for removing any contaminants which are harmful to the tissue culture process;
   (c) incubating the surface-sterilized explants at a temperature between 27° C. to 30° C. in the presence of about 3 klux white fluorescent light for 15 hrs. a day, in agarified medium-A for the plant explants of C. aurantifolia and medium B for the plant explants of C. siniensis, as defined in Table 1, for a period ranging between 20–30 days, to develop axillary buds and obtain 70–80% infection-free cultures of C. aurantifolia or C. sinensis;

(d) subculturing the explants of step (c) along with sprouted axillary buds at least 4 times, by sub-culturing the explants of C. aurantifolia in medium-A or C. sinensis in medium-B as defined in Table 1, to produce several aseptic fast-growing shoots;

(e) excising the meristem domes along with youngest 2–3 leaf primordia of length between 0.2–0.5 mm from the aseptically grown shoots and culturing the meristem domes in medium C as defined in Table 1, at a temperature between 27° C. and 30° C. in the presence of about 3 klux, white fluorescent light for a period of about 15 days to generate shoots of length of about 8 mm;

(f) subculturing the meristem-regenerated shoots on filter paper bridge employing liquid medium-D as defined in table 1, in order to obtain healthy shoots of an average length of about 1.5 cm without intervening callusing within a period of 20–25 days;

(g) proliferating the meristem-regenerated shoots of C. aurantifolia or C. sinensis by repeated subculture in medium-A or medium-B, respectively to obtain an average of about 6–10 well-developed shoots, within 4 subcultures of 30 days each;

(h) inducing roots in excised meristem-regenerated well-developed shoots of C. auranitifolia to the extent of about 100% in 15 days, or C. sinensis to the extent of about 90% in 25 days, in agarified media-E and F respectively;

(i) transferring the rooted shoots of C. sinenisis to medium-G as defined in Table 1, or allowing the shoots of C. aurantifolia to grow in medium A for a further period of 15 days in order to develop tap roots;

(j) hardening the rooted shoots ex-vitro in the liquid medium-H as defined in Table 1, for 10 days in a hardening chamber, wherein the relative humidity is lowered gradually from about 90% to about 60% under about 3 klux light intensity from white fluorescent tubes supplemented with light from incandescent lamps at 26° to 28° C. and allowing the rooted shoots to grow in the same medium, for 30 days; and (k) transferring the hardened rooted shoots to soil containing organic fertilizer for ex vitro growth at relative humidity of 90% to 60% at a temperature of 27° C. to 30° C. in the presence of white fluorescent light for a period of about 7 days to ensure 95% to 100% survival of the rooted shoots of Citrus species namely C. auranitifolia or C. sinensis.

2. A method as claimed in claim 1, wherein the explants are selected from the group consisting of shoot meristems having 2–3 leaf primordia which measure about 0.2 to 0.5 mm in length or single node stem segments.

3. A method as claimed in claim 1 wherein the explant is decontaminated by surface-sterilizing the nodal stem segments obtained from C. aurantifolia or C. sinensis, washing the said segments with tap water, followed by pre-treatment with about 5% detergent solution for 5 minutes, rinsing with distilled water followed by a quick dip in 95% ethanol and surface-sterilizing with 0.1% $HgCl_2$ solution for about 15 minutes and washing surface-sterilized nodal stem segments thoroughly with sterile distilled water followed by cutting off the internodal portions on either side of the node and preparing the explant for inoculation.

4. A method as claimed in claim 1 wherein the medium-A comprises:

| INGREDIENTS | CONCENTRATION (mg/L) |
| --- | --- |
| $(NH_4)_2SO_4$ | 250 |
| $NH_4NO_3$ | 1500 |
| $KH_2PO_4$ | 1500 |
| $CaCl_2.2H_2O$ | 150 |
| $MgSO_4.7H_2O$ | 400 |
| Fe-$Na_2$-EDTA*(ml $1^{-1}$) | 5 |
| $MnSO_4.4H_2O$ | 20 |
| $ZnSO_4.4H_2O$ | 8 |
| $H_3BO_3$ | 6 |
| KI | 0.8 |
| $Na_2MoO_4$, $2H_2O$ | 0.2 |
| $CuSO_4.5H_2O$ | 0.02 |
| $CoCl_2.6H_2O$ | 0.02 |
| Thiamine-HCl | 0.2 |
| Pyridoxine-HCl | 0.1 |
| Nicotinic acid | 0.5 |
| Ascorbic acid | 10 |
| m-Inositol | 100 |
| Adenine sulphate | 15 |
| BAP | 0.25 |
| IAA | 0.25 |
| Malt Extract | 500 |
| Sucrose (%) | 5 |
| pH | 5.8 |
| Agar (%) | 0.75 |

5. A method as claimed in claim 1 wherein the medium-B comprises:

| INGREDIENTS | CONCENTRATION (mg/L) |
| --- | --- |
| $KH_2PO_4$ | 250 |
| Adenine sulphate | 25 |
| NAA | 0.5 |
| $(NH_4)_2SO_4$ | 250 |
| $NH_4NO_3$ | 1500 |
| $KNO_3$ | 1500 |
| $KH_2PO_4$ | 150 |
| $CaCl_2.2H_2O$ | 400 |
| $MgSO_4.7H_2O$ | 450 |
| Fe-$Na_2$-EDTA*(ml $1^{-1}$) | 5 |
| $MnSO_4.4H_2O$ | 20 |
| $ZnSO_4.4H_2O$ | 8 |
| $H_3BO_3$ | 6 |
| KI | 0.8 |
| $Na_2MoO_4$, $2H_2O$ | 0.2 |
| $CuSO_45H_2O$ | 0.02 |
| $CoCl_2.6H_2O$ | 0.02 |
| Thiamine-HCl | 0.2 |
| Pyridoxine-HCl | 0.1 |
| Nicotinic acid | 0.5 |
| Ascorbic acid | 10 |
| m-Inositol | 100 |
| Adenine sulphate | 15 |
| BAP | 0.25 |
| IAA | 0.25 |
| Malt Extract | 500 |
| Sucrose (%) | 5 |
| pH | 5.8 |
| Agar (%) | 0.75 |

6. A method as claimed in claim 1 wherein the medium-C comprises:

| INGREDIENTS | CONCENTRATION (mg/L) |
|---|---|
| $(NH_4)_2SO_4$ | 250 |
| $NH_4NO_3$ | 1500 |
| $KNO_3$ | 1500 |
| $KH_2PO_4$ | 150 |
| $CaCl_2.2H_2O$ | 400 |
| $MgSO_4.7H_2O$ | 450 |
| $Fe-Na_2\text{-EDTA}*(ml\ 1^{-1})$ | 5 |
| $MnSO_4.4H_2O$ | 20 |
| $ZnSO_4.4H_2O$ | 8 |
| $H_3BO_3$ | 6 |
| KI | 0.8 |
| $Na_2MoO_4, 2H_2O$ | 0.2 |
| $CuSO_4.5H_2O$ | 0.02 |
| $CoCl_2.6H_2O$ | 0.02 |
| Thiamine-HCl | 0.2 |
| Pyridoxine-HCl | 0.1 |
| Nicotinic acid | 0.5 |
| Ascorbic acid | 10 |
| m-Inositol | 100 |
| Adenine sulphate | 15 |
| IAA | 0.1 |
| GA | 5 |
| Sucrose (%) | 3 |
| pH | 5.8 |
| Glycine | 3 |
| L-Glutamine | 25 |
| L-Arginine | 15 |
| L-Asparagine | 10 |
| L-Lysine | 10 |
| L-Cysteine | 10 |

7. A method as claimed in claim 1 wherein medium-D comprises:

| INGREDIENTS | CONCENTRATION (mg/L) |
|---|---|
| $(NH_4)_2SO_4$ | 250 |
| $NH_4NO_3$ | 1500 |
| $KNO_3$ | 1500 |
| $KH_2PO_4$ | 150 |
| $CaCl_2.2H_2O$ | 400 |
| $MgSO_4.7H_2O$ | 450 |
| $Fe-Na_2\text{-EDTA}*(ml\ 1^{-1})$ | 5 |
| $MnSO_4.4H_2O$ | 20 |
| $ZnSO_4.4H_2O$ | 8 |
| $H_3BO_3$ | 6 |
| KI | 0.8 |
| $Na_2MoO_4, 2H_2O$ | 0.2 |
| $CuSO_4.5H_2O$ | 0.02 |
| $CoCl_2.6H_2O$ | 0.02 |
| Thiamine-HCl | 0.2 |
| Pyridoxine-HCl | |
| Nicotinic acid | 0.5 |
| Ascorbic acid | 10 |
| m-Inositol | 100 |
| Adenine sulphate | 15 |
| BAP | 0.1 |
| IAA | 1 |
| GA | 10 |
| Malt Extract | 100 |
| Sucrose (%) | 3 |
| pH | 5.8 |
| Glycine | 3 |
| L-Glutamine | 25 |
| L-Arginine | 15 |
| L-Asparagine | 10 |
| L-Lysine | 10 |
| L-Cysteine | 10 |

8. A method as claimed in claim 1 wherein the medium-E comprises:

| INGREDIENTS | CONCENTRATION (mg/L) |
|---|---|
| $(NH_4)_2SO_4$ | 100 |
| $NH_4NO_3$ | 300 |
| $KNO_3$ | 500 |
| $KH_2PO_4$ | 150 |
| $CaCl_2.2H_2O$ | 100 |
| $MgSO_4.7H_2O$ | 100 |
| $Fe-Na_2\text{-EDTA}*(ml\ 1^{-1})$ | 5 |
| $MnSO_4.4H_2O$ | 20 |
| $ZnSO_4.4H_2O$ | 8 |
| $H_3BO_3$ | 6 |
| KI | 0.8 |
| $Na_2MoO_4, 2H_2O$ | 0.2 |
| $CuSO_4.5H_2O$ | 0.02 |
| $CoCl_2.6H_2O$ | 0.02 |
| Thiamine-HCl | 0.2 |
| Pyridoxine-HCl | 0.1 |
| Nicotinic acid | 0.5 |
| Ascorbic acid | 10 |
| Adenine sulphate | 5 |
| IPA | 0.125 |
| IBA | 0.125 |
| Chlorogenic acid | 1 |
| Sucrose (%) | 3 |
| pH | 5.8 |
| Agar (%) | 0.75 |

9. A method as claimed in claim 1 wherein the medium-F comprises:

| INGREDIENTS | CONCENTRATION (mg/L) |
|---|---|
| $(NH_4)_2SO_4$ | 200 |
| $NH_4NO_3$ | 500 |
| $KNO_3$ | 500 |
| $KH_2PO_4$ | 250 |
| $CaCl_2.2H_2O$ | 200 |
| $MgSO_4.7H_2O$ | 300 |
| $Fe-Na_2\text{-EDTA}*(ml\ 1^{-1})$ | 5 |
| $MnSO_4.4H_2O$ | 20 |
| $ZnSO_4.4H_2O$ | 8 |
| $H_3BO_3$ | 6 |
| KI | 0.8 |
| $Na_2MoO_4, 2H_2O$ | 0.2 |
| $CuSO_4.5H_2O$ | 0.02 |
| $CoCl_2.6H_2O$ | 0.02 |
| Thiamine-HCl | 2.5 |
| Pyridoxine-HCl | 0.5 |
| Nicotinic acid | 0.5 |
| Riboflavin | 0.1 |
| Folic acid | 0.1 |
| d-Biotin | 0.1 |
| Ascorbic acid | 5 |
| Adenine sulphate | 5 |
| IAA | 1 |
| NAA | 0.5 |
| IPA | 0.5 |
| Chlorogenic acid | 1 |
| Sucrose (%) | 5 |
| pH | 5.8 |
| Agar (%) | 0.75 |
| Glycine | 3 |
| L-Arginine | 15 |

10. A method as claimed in claim 1 wherein the medium-G comprises:

| INGREDIENTS | CONCENTRATION (mg/L) |
| --- | --- |
| $(NH_4)_2SO_4$ | 200 |
| $NH_4NO_3$ | 500 |
| $KNO_3$ | 500 |
| $KH_2PO_4$ | 250 |
| $CaCl_2.2H_2O$ | 200 |
| $MgSO_4.7H_2O$ | 300 |
| $Fe-Na_2-EDTA*(ml\ l^{-1})$ | 5 |
| $MnSO_4.4H_2O$ | 20 |
| $ZnSO_4.4H_2O$ | 8 |
| $H_3BO_3$ | 6 |
| KI | 0.8 |
| $Na_2MoO_4, 2H_2O$ | 0.2 |
| $CuSO_4.5H_2O$ | 0.02 |
| $CoCl_2.6H_2O$ | 0.02 |
| Thiamine-HCl | 2.5 |
| Pyridoxine-HCl | 0.5 |
| Nicotinic acid | 0.5 |
| Riboflavin | 0.1 |
| Folic acid | 0.1 |
| d-Biotin | 0.1 |
| Ascorbic acid | 5 |
| Adenine sulphate | 5 |
| IAA | 0.25 |
| Chlorogenic acid | 1 |
| Sucrose (%) | 5 |
| pH | 5.8 |
| Agar (%) | 0.75 |

-continued

| INGREDIENTS | CONCENTRATION (mg/L) |
| --- | --- |
| Glycine | 3 |
| L-Arginine | 15 |

11. A method as claimed in claim 1 wherein the medium-H comprises:

| INGREDIENTS | CONCENTRATION (mg/L) |
| --- | --- |
| $NH_4NO_3$ | 500 |
| $KNO_3$ | 250 |
| $KH_2PO_4$ | 125 |
| $Ca(NO_3)_2.4H_2O$ | 500 |
| $MgSO_4.7H_2O$ | 250 |
| $Fe-Na_2-EDTA*(ml\ l^{-1})$ | 3 |
| $MnSO_4.4H_2O$ | 20 |
| $ZnSO_4.4H_2O$ | 8 |
| $H_3BO_3$ | 6 |
| KI | 0.8 |
| $Na_2MoO_4,2H_2O$ | 0.2 |
| $CuSO_4.5H_2O$ | 0.02 |
| $CoCl_2.6H_2O$ | 0.02 |

* * * * *